(12) United States Patent
Asay et al.

(10) Patent No.: US 6,800,487 B1
(45) Date of Patent: Oct. 5, 2004

(54) METHOD FOR MONITORING THE CRYSTALLIZATION OF AN ORGANIC MATERIAL FROM A LIQUID

(75) Inventors: Blaine W. Asay, Los Alamos, NM (US); Bryan F. Henson, Los Alamos, NM (US); Robert K. Sander, Los Alamos, NM (US); Jeanne M. Robinson, Los Alamos, NM (US); Steven F. Son, Los Alamos, NM (US); Peter M. Dickson, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 91 days.

(21) Appl. No.: 10/259,345

(22) Filed: Sep. 26, 2002

Related U.S. Application Data

(63) Continuation-in-part of application No. 09/493,645, filed on Jan. 28, 2000, now Pat. No. 6,465,255.
(60) Provisional application No. 60/117,900, filed on Jan. 29, 1999.

(51) Int. Cl.[7] .............................................. G01N 21/75
(52) U.S. Cl. .......................... 436/164; 436/4; 252/582; 356/30; 356/446
(58) Field of Search ..................... 436/164, 4; 252/582; 356/30, 446

(56) References Cited

U.S. PATENT DOCUMENTS

| | | | | |
|---|---|---|---|---|
| 3,820,087 A | * | 6/1974 | Chaudhari et al. | 365/113 |
| 4,810,789 A | * | 3/1989 | Behme et al. | 544/230 |
| 5,015,646 A | * | 5/1991 | Simms | 514/252.15 |
| 5,352,388 A | * | 10/1994 | Seddon et al. | 252/582 |
| 5,786,448 A | * | 7/1998 | Nefzi et al. | 530/317 |

OTHER PUBLICATIONS

S. F. Son, B. W. Asay, B. F. Henson, R. K. Sander, A. N. Ali, P. M. Zielinski, D. S. Phillips, R. B. Schwarz, and C. B. Skidmore, "Dynamic Observation of a Thermally Activated Structure Change in 1,3,5–Triamino–2,4,6–Trinitrobenzene (TATB) by Second Harmonic Generation," J. Phys. Chem. B, vol. 103, No. 26, pp. 5434–5440, Jun. 1999.

R. J. Karpowicz, L. S. Gelfand, and T. B. Brill, "Application of Solid–Phase Transition Kinetics to the Properties of HMX," AIAA Journal, vol. 21, No. 2, pp. 310–311, May 1982.

B. F. Henson, K. R. Wilson, and J. M. Robinson, "Quantitative Measurements of Multilayer Physical Adsorption on Heterogeneous Surfaces from Nonlinear Light Scattering," Physical Review Letters, vol. 79, No. 8, pp. 1531–1534, Aug. 1997.

Dale J. LeCaptain and Kris A. Berglund, "The Applicability of Second Harmonic Generation for In situ Measurement of Induction Time of Selected Crystallization Systems," Journal of Crystal Growth, 203, pp. 564–569, 1999.

R. Cameroni, M. T. Bernabei, F. Forni, G. Coppi, "Polymorphism of Chloramphenicol Stearate," Farmaco Edizione Pratica, vol. 33, fasc. 10, pp. 447–454, 1978.

(List continued on next page.)

*Primary Examiner*—Jill Warden
*Assistant Examiner*—Monique T. Cole
(74) *Attorney, Agent, or Firm*—Samuel L. Borkowsky

(57) ABSTRACT

Method for monitoring the crystallization of at least one organic material from a liquid. According to the method, a liquid having at least one organic material capable of existing in at least one non-centrosymmetric phase is prepared. The liquid is interrogated with a laser beam at a chosen wavelength. As at least a portion of the at least one organic material crystallizes from the liquid, the intensity of any light scattered by the crystallized material at a wavelength equal to one-half the chosen wavelength of the interrogating laser beam is monitored. If the intensity of this scattered light, increases, then the crystals that form include at least one non-cetrosymmetric phase.

10 Claims, 4 Drawing Sheets

OTHER PUBLICATIONS

Israel Goldberg and Yigal Becker, "Polymorphs of Tamoxifen Citrate: Detailed Structural Characterization of the Stable Form," Journal of Pharmaceutical Sciences, vol. 76, No. 3, pp. 259–264, Mar. 1987.

Laszlo Borka and John K. Haleblian, "Crystal Polymorphism o fPharmaceuticals," Acta Pharm. Jugosl., vol. 40, No. 1–2, pp. 71–94,1990.

B. F. Henson. B. W. Asay, R. K. Sander, S. F. Son, J. M. Robinson, and P. M. Dickson, "Dynamic Measurement of the HMX$\beta$–$\delta$ Phase Transition by Second Harmonic Generation," Physical Review Letters, vol. 82, No. 6, pp. 1213–1216, Feb. 8, 1999.

* cited by examiner

US 6,800,487 B1

METHOD FOR MONITORING THE CRYSTALLIZATION OF AN ORGANIC MATERIAL FROM A LIQUID

RELATED APPLICATIONS

This application is a continuation-in-part of U.S. patent application Ser. No. 09/493,645 filed on Jan. 28, 2000 now U.S. Pat. No. 6,465,255 and claims the benefit of U.S. Provisional Application 60/117,900 filed on Jan. 29, 1999, both of which are hereby incorporated by reference.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to monitoring phase transitions in materials and, more particularly, to a method for monitoring the crystallization of an organic material from a liquid using second harmonic generation.

BACKGROUND OF THE INVENTION

By providing the appropriate thermal or mechanical input, phase transitions may be induced in materials. Phase transitions are generally identified by monitoring changes in a physical property or properties of the material during thermal and/or mechanical input. The elucidation of the phase transition behavior of a material is important in understanding the properties of the material. Thus, the development of methods for identifying and probing phase transitions in materials is of great interest.

Many materials, such as organic and inorganic compounds and polymers, exhibit polymorphism, i.e. they can exist in more than one crystallographically distinct crystalline phase. These crystalline phases, known as polymorphs, may be centrosymmetric phases that have inversion symmetry, or non-centrosymmetric crystalline phases that do not have inversion symmetry.

Although the individual polymorphs of a polymorphic material have the same chemical composition, they can have significantly different physical properties. This may be illustrated using, for example, the energetic, polymorphic organic compound octahydro-1,3,5,7-tetranitro-1,3,5,7-tetrazocine (HMX). Four distinct, crystalline phases (i.e. 4 polymorphs) have been identified for HMX. Two of these polymorphs, β-HMX and δ-HMX, differ in their sensitivity to temperature and pressure. The beta phase of HMX (β-HMX) is relatively insensitive to changes in temperature and pressure. However, explosive decomposition may be induced more readily in the delta phase of HMX (δ-HMX) with thermal and/or shock input.

Many important biologically active pharmaceutical compounds are polymorphic. The phase behavior and physical properties of polymorphic pharmaceutical compounds must be thoroughly understood, since the properties of the various polymorphs of a polymorphic pharmaceutical compound may be different. For example, individual polymorphs of a polymorphic pharmaceutical compound can exhibit different rates of dissolution, which can affect their concentration in body tissues and therefore their effectiveness. Examples of polymorphic pharmaceuticals include the anti-diabetic drug tolbutamide, the antibiotic chloramphenicol, and the selective estrogen response modulator tamoxifen. For a review of polymorphic pharmaceutical compounds, see L. Borka and J. K. Haleblian, Acta. Pharm. Jugosl. 40, 1 (1990) hereby incorporated by reference.

The development of crystallization procedures to induce the formation of a desired polymorph is usually expensive and time consuming. Optimizing these procedures usually involves determining operating temperatures, operating pressures, rates of heating or cooling, solvents, concentrations of materials, and other parameters. Rapid non-invasive, in-situ, dynamic monitoring during crystallization can provide important information regarding the formation of desired and undesired polymorphs of polymorphic materials. While calorimetry, Infrared and Raman spectroscopy, and x-ray diffraction have traditionally been used for the detection of polymorphic transitions, system costs are prohibitively expensive at the laboratory scale, and will likely limit their use in situ on the industrial scale.

It is extremely important to understand the phase behavior of polymorphic materials. Clearly, a rapid and sensitive method for identifying and probing the phase transitions of polymorphic materials is highly desirable.

Therefore, an object of the present invention is to provide a rapid and highly sensitive method for identifying and probing phase transitions of polymorphic materials.

Another object of the present invention is to provide a method for monitoring the crystallization of an organic material from a liquid.

Yet another object of the present invention is to provide a method for detecting the crystallization of centrosymmetric and non-centrosymmetric polymorphs.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention as embodied and broadly described herein, the invention includes a method for monitoring the crystallization of at least one organic material from a liquid. According to the method, a liquid having at least one organic material capable of existing in at least one non-centrosymmetric phase is prepared. The liquid is interrogated with a laser beam at a chosen wavelength. As at least a portion of the at least one organic material crystallizes from the liquid, the intensity of any light scattered by the crystallized material at a wavelength equal to one-half the chosen wavelength of the interrogating laser beam is monitored.

The invention also includes method of monitoring the crystallization of at least one organic material from a liquid reaction mixture during a chemical reaction. According to the method, a liquid reaction mixture is subjected to conditions that promote a chemical reaction that produces at least one crystalline organic material having at least one non-centrosymmetric phase. As the at least one crystalline organic material is produced, the liquid reaction mixture is interrogated with a laser beam at a chosen wavelength. Meanwhile, the intensity of any light scattered by the crystallized organic material is monitored at a wavelength equal to one-half the chosen wavelength of the interrogating laser beam.

BRIEF DESCRIPTION OF THE DRAWINGS

The accompanying drawings, which are incorporated in and form a part of the specification, illustrate embodiments of the present invention and, together with the description, serve to explain the principles of the invention.

In the Figures.

DETAILED DESCRIPTION OF THE INVENTION

Figure 1:
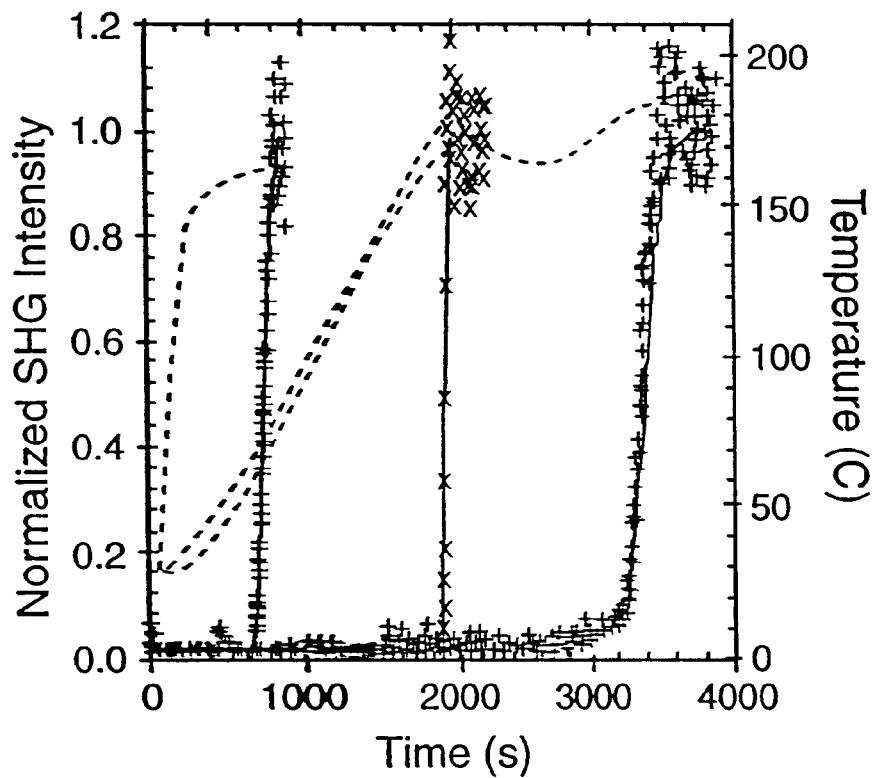
FIG. 1 is a graphical representation of a heating curve for HMX showing changes in SHG intensity and temperature versus time.

The present invention employs a pulsed coherent laser beam to rapidly probe a polymorphic organic material capable of existing in at least one non-centrosymmetric phase as the material crystallizes from a liquid. During crystallization, the liquid is interrogated with a pulsed laser beam, and scattered light having a wavelength of half the wavelength (twice the frequency) of the input beam is detected and measured. This scattered light arises from a non-linear optical process known as second harmonic generation (SHG), which occurs when high-intensity laser light interacts with a non-centrosymmetric crystalline lattice. According to the invention, the method may be used to detect the appearance of a non-centrosymmetric phase crystallizing from the liquid. As crystals having a non-centrosymmetric phase crystallize from the liquid, they are detected by detecting in increase in the intensity of the SHG signal. Crystals having a symmetric phase do not produce an SHG signal.

The method is a zero background method and therefore highly sensitive, since non-crystalline or crystalline centrosymmetric materials do not contribute to the SHG signal. The method is also rapid; it can make temporally resolved measurements on time scales of picoseconds and spatially resolved measurements in the micron range. The present invention thus provides an in situ, spatially and temporally resolved measurement of the presence or absence of a non-centrosymmetric phase of a polymorphic organic compound.

The crystallization of non-centrosymmetric phases can be monitored from a wide variety of liquid materials. The liquid could include a single organic compound, or a plurality of any number of organic compounds. Preferably, the liquid includes a major component of one organic compound, or organic polymer, capable of existing in a non-centrosymmetric phase. The liquid could also include one or more minor components that preferentially would not co-crystallize with the desired major component.

The major organic component may be, for example, a polymorphic organic compound capable of existing in a non-centrosymmetric phase and in one or more centrosymmetric phases. As the organic compound crystallizes, the detection of an increase in the SHG signal would indicate that the non-symmetric phase is crystallizing from the liquid. Alternatively, if the organic crystals are detected visually or some other way but the SHG signal does not increase, then those organic crystals likely do not include a non-centrosymmetric phase.

Liquids used with the present invention are not limited to the liquid phase of the material undergoing crystallization. The liquid could be a solution where the polymorphic organic material is dissolved in a solvent such as acetonitrile, dichloromethane, chloroform, methanol, hexane, water, and the like, or dissolved in a solvent system (chloroform/acetonitrile, for example).

The method of the invention may be used to monitor the crystallization of a product organic compound or organic polymer product formed during in a chemical reaction mixture in situ. The crude organic product may contain one organic compound, but typically includes several that usually have to be separated. The products, once separated, can be purified by recrystallization.

If the chemical reaction is well designed, the crude product consists essentially of a single organic compound. Often, the crude product contains impurities that must be separated from the desired organic compound. If the crude product is a mixture of organic compounds, a solvent or a solvent system is often used to separate the desired product from the other products. Recrystallization is often used as a purification procedure, especially when the major portion of the crude product is the desired organic compound. One or more recrystallization steps may then be used to obtain the is purified organic compound. For an effective recrystallization, a variety of solvents and/or solvent systems are tested first. Once a suitable solvent or solvent system is selected, the crude product is combined with the solvent or solvent system. Sometimes, the desired product dissolves and one or more impurities do not and can easily be removed by filtration. In this situation, the desired product may be crystallized from the remaining solution. Other times, the impurities dissolve and the desired component do not. In such a situation, the solution formed contains the impurities and the remaining undissolved solid contains the desired product and can then be recrystallized. Most likely, the desired product and one or more impurities will be soluble in the solvent/solvent system. The desired product will be the major component and will preferentially crystallize out, leaving the impurities in solution.

Crystallization may be induced by, for example, cooling a solution of the desired product until crystals of the desired product form. Crystallization may also be induced by removing solvent from the solution of the desired product until crystals form, by adding a cosolvent to the solution of the desired product that changes the dielectric constant of the solution so that the desired product is less soluble after cosolvent addition, etc.

It is not intended that the method of the invention be limited to any particular method of inducing crystallization. Any method capable of inducing crystallization from a liquid can be used. As crystallization occurs, the solution is interrogated with a laser beam at a chosen wavelength while the intensity of the SHG signal is monitored.

The procedure for monitoring an SHG signal from a liquid is essentially the same as the procedure for monitoring an SHG signal from a solid. To illustrate how the SHG signal may be monitored, a phase transition from the β-phase to the δ-phase was induced in the solid organic explosive HMX and this transition was observed by monitoring the SHG signal during the phase transition (the kinetics of this transition were also measured).

HMX exhibits a wide variety of behaviors when subjected to various thermal fields. Temperatures above 180° C. induce explosion after an induction time of $10^5$–$10^1$ seconds (s). IR laser irradiation generates surface temperatures from 500–700 K and ignition at $10^{-3}$–$10^1$ s. Shear or frictional heating of pressed solids to 700–900 K results in ignition in $10^{-4}$ s. Planar shocks from 10 GPa result in detonation over a time of about $10^{-7}$–$10^{-6}$ s.

It has been recognized for 30 years that the crystalline phases of HMX may play a role in the decomposition chemistry. Of the four phases of HMX identified, two have been of traditional concern, β-HMX, a low temperature form, and δ-HMX, a high temperature form that is the only phase observed upon low pressure heating of all four polymorphs. Differences in burn rate and drop-height sensitivity are known for the β-phase and for the δ-phases, with δ-HMX the more hazardous material. Kinetic measurements of the β-δ transition have shown that the first order activation energy and frequency factor resemble those attributed to chemical decomposition, supporting previous speculation that the initial decomposition step in HMX is coupled to, or preceded by, the formation of δ-HMX.

No in-situ measurements of the rate of the transformation have been reported for ignition experiments. Identification of the phase and transition rate have relied on traditional calorimetry, Fourier Transform Infrared Spectroscopy (FT-IR), and Raman techniques addressing times and temperatures of $10^{-2}$–$10^5$ s and 450–500 K. However, the role of the β-δ transition during ignition has remained uncertain, and the validity of extrapolating measured transition rates to ignition times of less than a second has not been established.

The β-δ transition was monitored by SHG during slow heating to verify that temperatures and times are consistent with established kinetics. The β-δ transition was then identified by SHG during a dynamic ignition experiment. The β-δ transition was observed at the surface of a pressed polycrystalline sample during laser irradiation at a wavelength of about 10.6 μm (20 Watts/cm²-s) prior to ignition. The transition time and surface temperature were consistent with low temperature measurements, validating the extrapolation of calculated transition rates to times of $10^{-2}$ s.

SHG was observed both in transmission through a thin layer of powdered crystal and in reflection from the surface of a pressed polycrystalline pellet. The relative SHG cross sections from β-HMX and δ-HMX were measured, and the phase transition was observed during slow heating. Powdered crystalline samples of a $KH_2PO_4$ (KDP) standard, and β- or δ-HMX (1–500 μm diameter) were mounted as thin layers of powder (about 500 μm thick) between sapphire windows of a cell. This cell was enclosed in an oven and placed in the optical path of a 10 Hz Nd:YAG laser light beam delivering 10 nanosecond (ns) pulses at 1064 nanometers (nm), (10–100 MW/cm²). Diffuse forward-scattered SHG light was filtered to remove the 1064 nm fundamental light, focused into a monochrometer, and detected with a phototube. The scattered intensity followed the square of the input intensity, with no strong dependence on input or detection polarization. The spectra of SHG from the δ-HMX and KDP were centered at 532 nm and consistent with the elastic conversion of the 1064 nm input pulse to 532 nm. Illumination of KDP samples with an intensity of 24 MW/cm² led to generation of 532 nm consistent with the large KDP cross section. By contrast, the SHG from β-HMX was lower by a factor of 50 relative to δ-HMX. This is consistent with the crystallographic symmetry of the two polymorphs, with β-HMX a centrosymmetric, monoclinic structure of $P2_1/c$ space group, and δ-HMX a non-centrosymmetric, hexagonal structure of space group $P6_222$. Thus, SHG in the β polymorph should thus be strongly suppressed relative to the δpolymorph due to symmetry considerations, and this is what is observed.

Additionally, the two polymorphs (i.e. β-HMX and δ-HMX) differ in several other respects. There is a 7% volume expansion on transformation from β-HMX to δ-HMX, and a change in unit cell participation from 2 molecules in β-HMX to 6 in δ-HMX. Also, the very polar nitro groups are nearly trans in the β polymorph (β-HMX) and cis in the δ polymorph (δ-HMX), leading to a significant change in dipole moment and reduction of molecular point group symmetry upon transition. For applications relating to thermal decomposition of energetic materials, this difference in cross-section between β-HMX and δ-HMX provides excellent contrast as an in-situ probe in dynamic experiments. This is a non-resonant application of SHG and therefore does not provide spectroscopic identification of any specific HMX phase. With their identification already established, the contrast in cross-section between the β polymorph and the δ polymorph allows the use of the SHG intensity to measure the rate of transformation between them.

FIG. 1 shows a graphical representation of data obtained from slow heating of three samples of β-HMX. The data are plotted as the SHG intensity (symbols) normalized to maximum signal on the left axis, and the temperature (dashed lines) on the right axis, both as a function of time. The transition from β-HMX to δ-HMX is apparent as a rapid increase in the SHG, occurring at temperatures of about 170° C. If one considers the normalized SHG intensity, varying from 0–1, as proportional to the δ-HMX mole fraction, these data may be modeled using the kinetic first order rate law below:

$$\frac{dc}{dt} = k(\beta_0 - c)(\delta_0 + c)$$

The above rate law is first order in both β and δ; c is the concentration of δ-HMX formed, $\beta_0$ and $\delta_0$ are the initial concentrations of β-HMX and δ-HMX respectively, it is the time and k is an Arrhenius rate expression, $k = A \times EXP(-E_a/RT)$.

The partially integrated rate law, normalized to $\beta_0$, is $$x(T, t) = \frac{fEXP[\beta_0 \int k(T, t) dt]}{fEXP[\beta_0 \int k(T, t) dt] + 1}$$

where x is the fraction of β-HMX converted to δ-HMX, and f is the initial ratio of δ-HMX to β-HMX, $\delta_0/\beta_0$. The normalized SHG intensity can then be expressed as a function of the δ-HMX fraction and a constant, e, which is the ratio of SHG intensity from pure β- and δ-HMX, shown below:

$$\frac{I_{2\omega}}{I_{2\omega}^{max}} = [\varepsilon(1 + x) + x]^2$$

The solid lines in FIG. 1 for each curve were calculated with these formulae, utilizing $E_a$, A, and f as fitting parameters. The optimized parameters were $E_a$=201.6(2.0) kJ/mol, log (A)=21.9(0.8), A in $cm^3$/g-s, and log(f)=−2.6(1.0), with the standard deviation at 95% confidence in parenthesis. Others have observed approximate first order behavior for the transition at low levels of conversion and determined the Arrhenius parameters to be Ea=204(2.0) kJ/mol, log(A)= 19.9(1.0) 1/s, with uncertainty in parenthesis. Observation of complete conversion leads to the use of a second order rate law. Our observations are consistent with what others have observed, and serve to quantify the observed SHG as a kinetic probe, yielding Arrhenius parameters consistent with those observed previously, and the assignment of a second order HMX rate law to the process. In addition, although kinetic measurements have been performed for all four phases of HMX, δ-HMX was the only product observed during heating at low pressure. We rely on these and subsequent observations to assign the transition observed here to the β-δ HMX transition.

Figure 2:
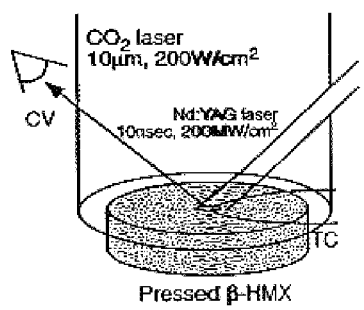
FIG. 2 is a schematic representation of the configuration used for the laser ignition of HMX.
Figure 3:
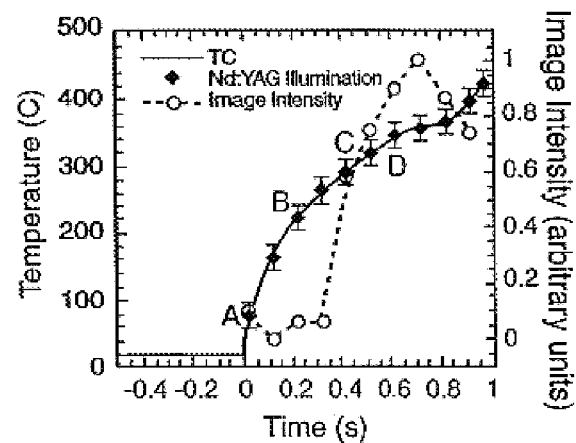
FIG. 3 is a graphical representation of the average image intensity and the temperature as a function of time relating to the laser ignition of HMX.
Figure 4:
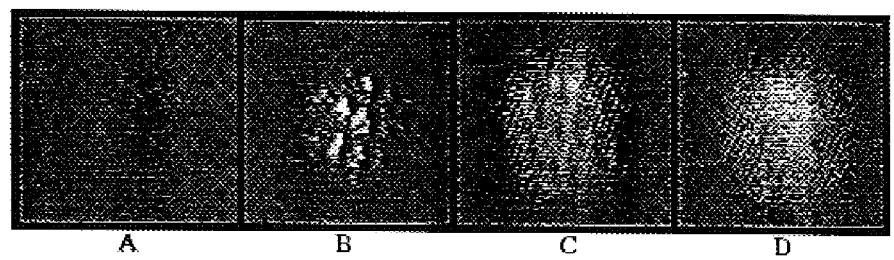
FIG. 4 shows selected SHG images during the β-δ HMX transition.

The configuration used for the laser ignition of HMX is shown in FIG. 2. A pressed pellet of HMX is illuminated by the continuous output of a $CO_2$ laser at a wavelength of about 10.6 μm. Interference effects from beam integration result in a cross-hatched pattern of slight surface temperature variability. A laser beam from a 10 Hz Nd:YAG laser, identical to the previous description, was directed onto the surface at an angle of about 30 degrees from normal, and a color video camera was used to image the SHG light at the surface along the specular reflection axis of the 1064 nm illumination. A 13 μm diameter thermocouple (type K), centered at the 1064 nm illumination spot on the surface, was used to record the temperature during heating. The $CO_2$ illumination was begun at time t=$t_0$, and the temperature rise was monitored until ignition in the gas phase approximately one second later. During heating, the SHG emission from the surface was imaged at the video rate of 60 Hz. A graphical representation of the temperature and the average image intensity as a function of time is shown in FIG. 3. Selected images of SHG appearance are shown FIG. 4. FIG. 3 shows the temperature recorded by the thermocouple as a function of time. The letters shown along the curve in FIG. 3 correspond to those below selected images in FIG. 4 and indicate the time and temperature at which the images of FIG. 4 were recorded. The images are from the video record of the 1064 nm illumination spot. SHG first appears at approximately 250 milliseconds (ms), with an uncertainty from the framing rate of 30 ms, and clearly reflects the cross hatched heating pattern on the surface. The appearance of the SHG indicates the transition from β-HMX to δ-HMX at the surface and from the average intensity of the video image. The transition time is determined to be 366(100) ms at a homogeneous surface temperature of 277(30) ° C.

Figure 5:
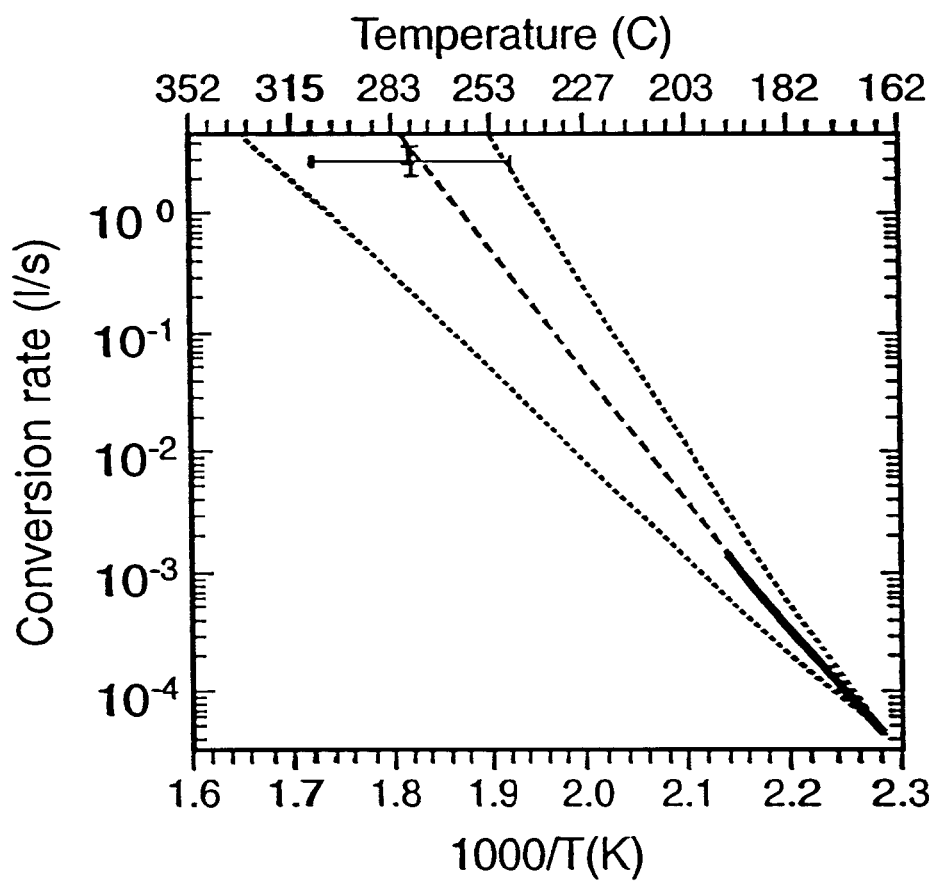
FIG. 5 is an Arrhenius plot of the observed β-δ HMX transition kinetics.

An Arrhenius plot of the observed β-δ transition kinetics is shown in FIG. 5. The solid bar is an average data observed by others. The dashed lines reflect the uncertainties in rate at higher temperatures that result from extrapolation of data with the reported uncertainties. The data point that results from this work is plotted as the inverse of the time to transition as a function of inverse temperature and is clearly consistent with the low temperature measurements. This verifies the extrapolation of these kinetics to combustion regimes that were first discussed many years ago. To our knowledge, the method of the present invention has provided the first measurements of a crystalline phase during a dynamic ignition.

Phase transitions in other polymorphic materials were also probed by monitoring the intensity of the SHG signal. These materials included 1,3,5-triamino-2,4,6-trinitrobenzene (TATB), 2,4,6,8,10,12-hexanitro-2,4,5,8,10,12-hexaazatetracyclo[$5.5.0.0.^{5,9}0.^{3,11}$]dodecane (CL-20), and a proprietary pharmaceutical material.

The method can be used to identify and probe phase transitions in polymorphic crystals having at least one non-centrosymmetric phase capable of second harmonic generation upon interrogation with a laser beam. The invention can be used to identify and probe phase transition behavior in polymorphic materials such as, for example, organic compounds having pharmaceutical activity, inorganic compounds, and polymers. The invention can also be used to provide kinetic information, such as the rates of transition of one polymorph to another. The invention can be used to identify and probe phase transitions during the crystallization of polymorphic pharmaceuticals to monitor the production of non-centrosymmetric crystalline phases during the crystallization process. Crystallizations may include crystallizations from solid powders, from liquid phases of polymorphic materials, and from solutions of the dissolved polymorphic materials. Crystallization from solution can involve dissolving a polymorphic solid in a solvent and crystallizing a desired polymorph from the solution by lowering the temperature of the solution, by removing solvent, by adding a crystallizing agent such as a co-solvent, etc. The solution is interrogated with a laser beam during crystallization to monitor the intensity of second-harmonic-generated light.

The method of the present invention includes a rapid and extremely sensitive dynamic method for monitoring the crystallization of non-centrosymmetric phases of polymorphic materials. We have demonstrated that the method is rapid and sensitive enough to identify a phase transition in an energetic organic compound immediately prior to explosive decomposition. The invention can provide images of a non-crystalline polymorph in the presence of other polymorphs, which makes it useful for quality control applications such as for optimization processing conditions for crystallization. The procedure is faster and typically more sensitive than Raman techniques. The invention also provides advantages over infrared techniques. While infrared spectral differences between crystalline polymorphs are often subtle, differences in SHG between centrosymmetric and non-centrosymmetric polymorphs can be much more easily detected. Also, in contrast to analytical techniques such as calorimetry and x-ray scattering, the present invention does not require a special sample preparation step.

The following example illustrates how the invention can be used to monitor the crystallization of a polymorphic pharmaceutical compound, the important antiestrogenic agent tamoxifen citrate. See, for example, I. Goldberg and Y. Becker in J. Pharmaceutical Sciences, vol. 76, pp. 259 (1987), hereby incorporated by reference. According to Goldberg, tamoxifen citrate exists in a stable form (B, in Goldberg) and in a metastable form (A, in Goldberg). The crystallographic space group for stable form B is centrosymmetric group $P2_1$/c, which should exhibit no SHG activity. The crystallographic space group for metastable form A is not known but is believed to be of lower symmetry. If metastable form A is noncentrosymmetric, then it should exhibit SHG activity. The practice of the invention may be illustrated for tamoxifen citrate in several ways. Firstly, metastable form A could be crystallized from a solution of tamoxifen citrate according to the crystallization procedure described by Goldberg et al. and during the crystallization, laser interrogation could be performed according to the method of the present invention. The invention could be used to provide at least a partial determination of the structure of form A, which would depend on whether or not a significant SHG signal is observed. A significant SHG signal would indicate that form A has crystallized into a structure having a lack of inversion symmetry. Furthermore, after determining the strength of the SHG signal in form A, the invention could then be used to monitor the crystallization of form A in any subsequent crystallization or recrystallization process where form A or form B is the desired product. This way, the invention could be used in the determination of the conditions for isolating form B, and for a system for monitoring the crystallization process to ensure quality control on a small scale, on a pilot plant scale, and ultimately on an industrial scale.

Figure 6A:
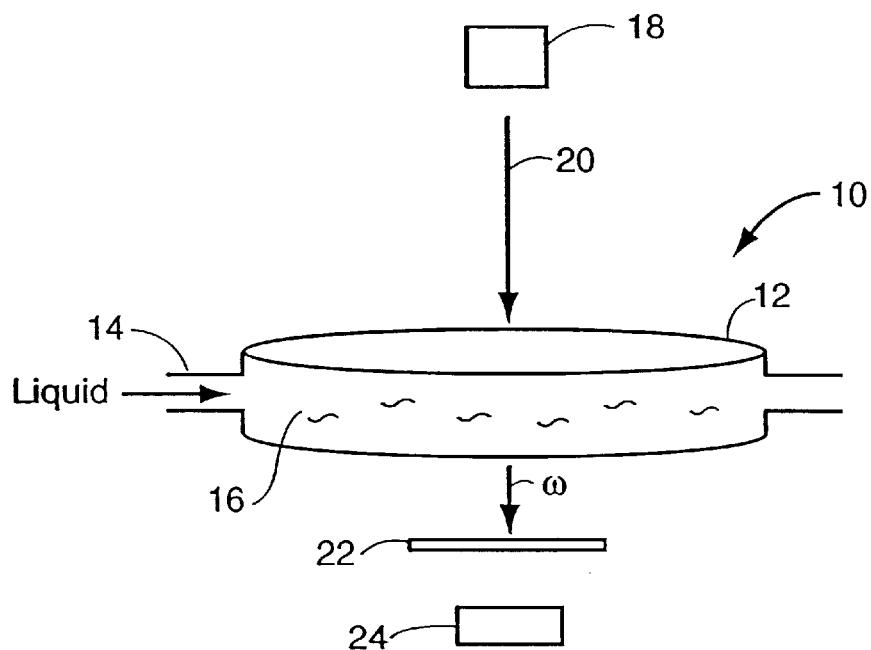
FIGS. 6a–b shows schematic representations of an apparatus demonstrating the method of the invention.
Figure 6B:
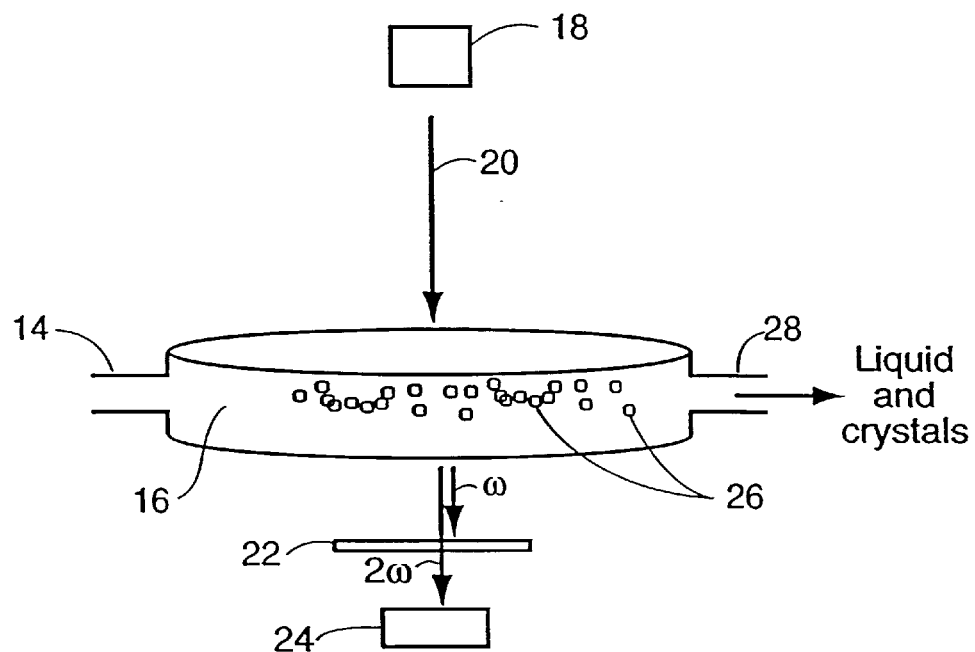

FIGS. 6a–b shows schematic representations of an apparatus demonstrating the method of the invention. Apparatus 10 includes container 12 with inlet 14 for receiving for receiving liquid 16. Apparatus 10 also includes laser 18, which delivers an incoming pulsed laser beam 20 having a wavelength $\omega$ to liquid 16 inside container 12. Laser beam 20 passes though liquid 16 and exits container 12. Apparatus 10 also includes filter 22 and detector 24. Filter 22 prevents light having a wavelength w from reaching detector 24 but passes SHG light at a wavelength $2\omega$ and allows this SHG light to reach detector 24. As FIG. 6a shows, no crystals have yet formed and so all of the laser light exiting container 12 is stopped by filter 22. FIG. 6b shows crystals 26 forming inside container 12. At least some of these crystals generate SHG light at a wavelength of 2w. The SHG light passes through filter 22 and is detected by detector 24. At a desired time, the contents of container 12 may be expelled through outlet 28.

The above examples of the present invention have been presented for purposes of illustration and description and are not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for monitoring the crystallization of at least one organic material from a liquid, comprising:
   (a) preparing a liquid comprising at least one organic material capable of existing in at least one non-centrosymmetric phase;
   (b) interrogating the liquid with a laser beam at a chosen wavelength;
   (c) crystallizing from the liquid at least a portion of the at least one organic material; and
   (d) monitoring the intensity of light scattered by the crystallizing organic material at a wavelength equal to one-half the wavelength of the chosen wavelength of the interrogating laser beam as the organic material crystallizes from the liquid.

2. The method of claim 1, wherein the liquid comprises at least one solvent.

3. The method of claim 1, wherein the at least one organic material is selected from the group consisting of organic compounds and organic polymers.

4. The method of claim 3, wherein the organic material comprises at least one polymorphic organic compound having pharmaceutical properties.

5. The method of claim 3, wherein the at least one organic polymer comprises a polymorphic organic polymer.

6. A method of monitoring the crystallization of at least one organic material from a liquid reaction mixture during a chemical reaction, comprising the steps of:
   (a) subjecting a liquid reaction mixture to conditions that promote a chemical reaction that produces crystalline organic material comprising at least one non-centrosymmetric phase;
   (b) interrogating the liquid reaction mixture with a laser beam at a chosen wavelength; and
   (c) monitoring the intensity of any light scattered by the crystalline organic material at a wavelength equal to one-half the chosen wavelength of the interrogating laser beam as the organic material crystallizes from the liquid reaction mixture.

7. The method of claim 6, wherein the liquid reaction mixture comprises at least one solvent.

8. The method of claim 6, wherein the crystalline organic material is selected from the group consisting of organic compounds and organic polymers.

9. The method of claim 6, wherein the crystalline organic material comprises at least one polymorphic organic compound having pharmaceutical properties.

10. The method of claim 6, wherein the crystalline organic material is a polymorphic organic polymer.

* * * * *